United States Patent [19]

Gindler et al.

[11] 4,239,495

[45] Dec. 16, 1980

[54] DETERMINATION OF PROTEIN

[75] Inventors: E. Melvin Gindler; Nadine Miller, both of Rockford, Ill.

[73] Assignee: Sherwood Medical Industries Inc., St. Louis, Mo.

[21] Appl. No.: 11,226

[22] Filed: Feb. 12, 1979

[51] Int. Cl.$^3$ .................... G01N 33/16; C09K 3/00
[52] U.S. Cl. .................... 23/230 B; 252/408; 424/3
[58] Field of Search .................... 252/408; 23/230 B; 424/3

[56] References Cited

U.S. PATENT DOCUMENTS

| | | | |
|---|---|---|---|
| 3,533,749 | 10/1970 | Kleinman | 252/408 |
| 3,754,865 | 8/1973 | Gindler | 252/408 |
| 3,873,272 | 3/1975 | Wakefield | 252/408 |
| 3,884,637 | 5/1975 | Gindler | 252/408 |
| 3,915,643 | 10/1975 | Gindler | 252/408 |
| 3,947,250 | 3/1976 | Pollack | 252/408 |
| 4,023,933 | 5/1977 | Bradford et al. | 252/408 |

OTHER PUBLICATIONS

Sedmak, J. J., et al., Anal. Biochem., vol. 79, pp. 544–552 (May 1977).
Miyada, D., et al., Clin. Chem., vol. 18, No. 1, pp. 52–56 (1972).
Doumas, B., et al., Clin. Chim. Acta, vol. 31, pp. 87–96 (1971).

*Primary Examiner*—Teddy S. Gron
*Attorney, Agent, or Firm*—Wegner, Stellman, McCord, Wiles & Wood

[57] ABSTRACT

An aqueous reagent system for the quantitative determination of protein is disclosed. The system contains Coomassie Brilliant Blue G-250 dye, a monobasic strong acid having a $pK_a$ of less than 3 (e.g. HCl), a polybasic phosphonic acid (e.g. NTP), a water soluble, non-ionic surfactant characterized as being a block copolymer containing terminal polyethylene oxide segments separated by a polypropylene oxide segment. Preferably the system also contains a small amount of an alcohol such as methanol or ethanol.

14 Claims, No Drawings

DETERMINATION OF PROTEIN

The present invention relates to the quantitative determination of protein in a biologic fluid and, more particularly, to an improved protein determination using the dye Coomassie Brilliant Blue G-250.

Several methods are in current use for determining the amount of protein in serum, cerebrospinal fluid (CSF), and urine samples. Among these is the biuret method (Mokrasch and McGilvery, *J. Biol. Chem.* 221, p. 909). In this method, peptide structures containing at least two peptide linkages react with $Cu++$ in alkaline solution to form a violet colored chelate complex. The actual structure of this complex is unknown, but it is known that the carbonyl and imine groups of the peptide bonds are involved.

Lowry and his colleagues (*J. Lab. Clin. Med.* 39, 663) used a pretreatment of proteins with an alkaline copper solution similar to the above followed by addition of Folin-Ciocalteu reagent (contains lithium salts of phosphotungstic and phosphomolybdic acids). The color produced was a result of the reduction of the phosphotungstic and phosphomolybdic acids to molybdenum and tungsten blue by the Cu-protein complex and by the tryptophan and tyrosin of the protein. Lowry utilized this method as a sensitive procedure for cerebrospinal fluid proteins (CSF). It has since been found that an error of $6 \pm 3$ mg of protein per 100 ml CSF is present in the Lowry procedure due to the presence of nonprotein substances which react under the conditions of the assay. (Svensmark, *Scand J. Clin LaB Invest* 10:50).

Dye binding methods have also been used for several years in the determination of proteins. The technique involves a reaction in which a dye becomes bound to the protein. The formation of this dye-protein complex causes the dye to exhibit a change in its optical properties. This phenomenon has come to be known as the so-called "protein error of indicators" because a dye reagent which contains proper buffering can be made to exhibit the normal pH sensitive color change upon binding to the protein with no pH change. Currently the most prominent dye being used for in vitro is bromcresol green (see Gindler U.S. Pat. No. 3,884,637). HABA and methyl orange are two other lesser used dyes. Dye/protein complex formation using Coomassie Brilliant Blue G250 as the dye has also been disclosed (see Bradford U.S. Pat. No. 4,023,933). Whereas the bromcresol green, HABA, and methyl orange dyes bind almost exclusively to albumin, Coomassie Brilliant Blue will bind to the wide variety of proteins found in serum, cerebrospinal fluid and urine.

The procedure disclosed in the Bradford patent has many advantages including high sensitivity which permits the use of small sample size. Principal drawbacks are the effective lack of color stability for extended periods largely due to precipitation of the protein-dye complex, the failure to show substantially the same reactivity to different proteins, and the failure to follow Beer's law.

The objective of the present invention is to provide a system for the quantitative determination of protein which is based on Coomassie Brilliant Blue G-250 and has the advantages thereof identified in the Bradford patent and which, in addition, exhibits improved protein-dye color stability, substantially the same reactivity to different proteins, and also follows Beer's law.

In accordance with the present invention there is provided an aqueous reagent system for the quantitative determination of protein which contains Coomassie Brilliant Blue G-250 dye, a monobasic strong acid having a $pK_a$ of less than 3, a polybasic phosphonic acid, and a water soluble, nonionic surfactant characterized as being a block copolymer containing terminal polyethylene oxide segments separated by a polypropylene oxide segment. Preferably the system also contains a small amount of an alcohol such as methanol or ethanol.

In general, the system is provided as two aqueous components; one containing the dye and monobasic acid with the other containing the surfactant, polybasic acid, and alcohol. Each component has extended stability (about one year refrigerated) and when mixed to form the reagent system, the system itself is stable for up to about four months refrigerated.

Coomassie Brilliant Blue G-250 is a well known dye which can be structurally represented as follows:

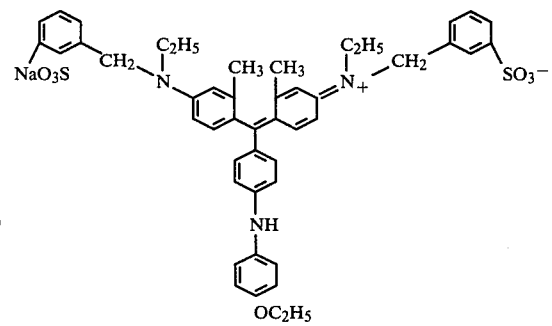

In the reagent system of the present invention, the dye will be present in an amount of about 0.001% to 0.1% (W/V), preferably 0.005% to 0.05% (W/V).

Useful monobasic acids have a $pK_a$ of less than 3 so that the reagent system has a pH of $-1$ to 1. Preferably the acid has a $pK_a$ of less than 2.5 and the system a pH of 0 to 1. Many useful monobasic acids are identified in the Bradford patent. Moreover, for the present invention, those highly ionized acids excluded by Bradford such as hydrochloric acid are preferred.

Nitrilotris (methylene) triphosphonic acid (NTP) is the preferred polybasic phosphonic acid and is a commercially available product. The combined amount of polybasic and monobasic acid in the system is about 1% to 15% (V/V), preferably about 2% to 5% (V/V) with the ratio of polybasic to monobasic acid being between about 2:1 to 3:1. The alcohol is present in an amount of up to about 10% (V/V), e.g. 0.1% to 10% (V/V), preferably about 0.1% to 2% (V/V).

As to the surfactant, those sold under the "Pluronic" tradename are useful herein. As identified in "Non-ionic Surfactants" (By I.R. Schmolka, Ed. Martin J. Schick, Marcel Decker Inc. 1967), the "Pluronics" have the structure $$HO(C_2H_4O)_a(C_3H_6O)_B(C_2H_4O)_cH$$

where b is at least 15, and $(C_2H_4O)_{a+c}$ is 20 to 90 percent of the total weight of the compound. "PLURONIC F-77" is preferred and is identified as having a polyoxypropylene base molecular weight of 2050 and a polyoxyethylene content by weight of 70%. The amount of surfactant included in the reagent is about 0.05% to 1% (W/V), preferably 0.1% to 0.25%.

The following example illustrates the present invention.

Preparation of Dye Component

Charge a glass vessel with about 800 ml of Deionized Water. Weigh out 120±1 mg of Coomassie Blue G-250 and transfer to the vessel. Apply vigorous stirring until completely dissolved. Measure out 27±0.5 ml of Conc. HCl (12M) and add slowly to the formulation vessel. Bring volume up to 1,000 ml with Deionized Water, stir well then filter through Whatman number 1 Filter Paper.

Preparation of Surfactant Component

Into a 100 cc volumetric flask place 2.14 gms of Pluronic F-77. Then measure out 14 ml of Deionized Water and transfer to the flask. Stir until all dissolved. Measure out 7.1 ml of Methanol and add this to the flask with continued stirring. Measure out 71.4 ml of NTP (50% aqueous solution) and add this to the vessel. Stir until a completely clear solution is obtained. Fill to 100 cc mark with Deionized Water, stir well.

Preparation of Reagent System (Working Reagent)

100.0 volumes of Dye Component is mixed with 14.0 volumes of Surfactant Component in a polyethylene bottle and incubated at 37° C. for 16-24 hours. A closed incubator oven is used. The Working Reagent is stored at 2°-8° C. and is stable at least four months when refrigerated.

Analysis of Specimens Using Reagent System

Sampe Size:
Urine—0.5 ml
Cerebrospinal Fluid—0.05 ml
Serum—0.05 ml after a 100 to 1 dilution with saline

Procedure

1. Centrifuge samples for 10 minutes at high speed to remove cells.
2.
   (A) Into a glass test tube (16×100 mm) place isotonic saline in specimen size for reagent blank.
   (B) Into individual glass test tubes place sample in indicated volume.
3. To each tube add 4.0 ml of Reagent System. Mix well with vortex mixer.
4. Place all test tubes in a rack. Immerse test tube rack in 37° C. incubation bath for 20 minutes.
5. Remove test tube rack from incubation bath and immerse in cold water bath (20°-25° C.) for 2-3 minutes.
6. With the wavelength of the spectrophotometer set at 610 nm, set the absorbance of the instrument to zero with the Reagent Blank and determine absorbance values of samples. The developed color is stable for 90 minutes. The amount of protein can be calculated or read from a calibration graph using information obtained from standards containing known protein concentrations. Calibrator solutions are run in the same manner as are unknown samples.

We claim:

1. An aqueous reagent system for the quantitative determination of protein, said reagent system having a pH of between about 0 and 1 and comprising a dye structurally represented as:

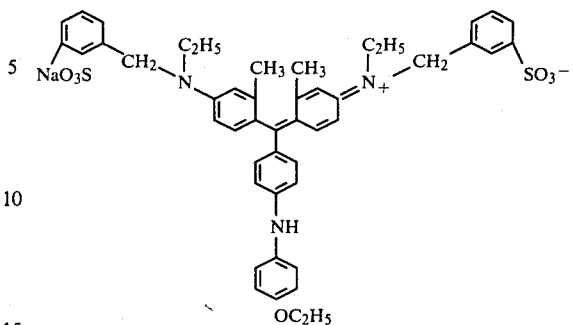

a monobasic strong acid having a $pK_a$ of less than 3, a polybasic phosphonic acid, and a water soluble, non-ionic surfactant characterized as being a block copolymer containing terminal polyethylene oxide segments separated by a polypropylene oxide segment, said ingredients being present in an amount such that said system exhibits substantially the same reactivity to different proteins and, when mixed with a protein containing sample, forms a stable colored protein dye complex which follows Beer's law.

2. The system of claim 1 containing, in addition, a small amount of alcohol.

3. The system of claim 2 wherein the monobasic acid is HCl, the polybasic acid is nitrilotris (methylene) triphosphonic acid, and the alcohol is methanol.

4. The system of claim 1 wherein the surfactant has the structure

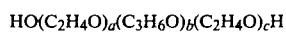

where b is at least 15 and a and c are selected such that ($C_2H_4O$) is between about 20 and 90 percent of the total weight of the compound.

5. The system of claim 4 wherein, in the surfactant, the polyoxypropylene base molecular weight is about 2050 and the polyoxyethylene content is about 70% by weight.

6. The system of claims 1, 2, 3, 4, or 5 wherein the ingredients are present in the following amounts:
   (a) the dye—0.005% to 0.05% (W/V),
   (b) combined polybasic and monobasic acids—2% to 5% (V/V) with the ratio of said polybasic acid to said monobasic acid being between about 2:1 and 3:1,
   (c) surfactant—0.1% to 0.25% (W/V).

7. The system of claim 6 wherein alcohol is present in an amount of between about 0.1% and 2% (V/V).

8. A method of assaying protein which comprises the steps of:
   (a) mixing a protein-containing sample with an aqueous reagent system having a pH of between about 0 and 1, said reagent system comprising a dye structurally represented as:

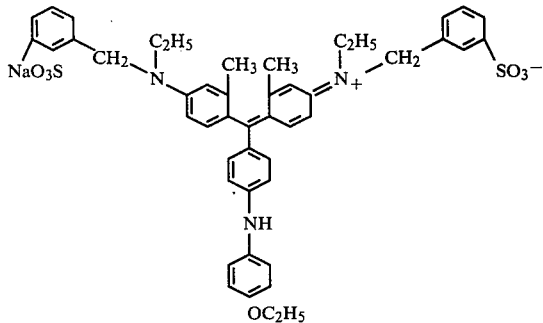

a monobasic strong acid having a $pK_a$ of less than 3, polybasic phosphonic acid, and a water soluble, nonionic surfactant characterized as being a block copolymer containing terminal polyethylene oxide segments separated by a polypropylene oxide segment, said ingredients being present in an amount such that said system exhibits substantially the same reactivity to different proteins and, when mixed with said protein-containing sample, forms a stable colored protein-dye complex which follows Beer's law, and (b) observing the resultant color change in said sample.

9. The method of claim 8 wherein said reagent system additionally contains a small amount of alcohol.

10. The method of claim 9 wherein the monobasic acid is HCl, the polybasic acid is nitrilotris (methylene) triphosphonic acid, and the alcohol is methanol.

11. The method of claim 8 wherein the surfactant has the structure $HO(C_2H_4O)_a(C_3H_6O)_b(C_2H_4O)_c$ where b is at least 15 and a and c are selected such that $(C_2H_4O)$ is between about 20 and 90 percent of the total weight of the compound.

12. The method of claim 11 wherein, in the surfactant, the polyoxypropylene base molecular weight is about 2050 and the polyoxyethylene content is about 70% by weight.

13. The method of claims 8, 9, 10, 11 or 12 wherein the ingredients of said reagent system are present in said reagent system in the following amounts:
 (a) the dye—0.005% to 0.05% (W/V);
 (b) combined polybasic and monobasic acids—2% to 5% (V/V) with the ratio of said polybasic acid to said monobasic acid being between about 2:1 and 3:1; and
 (c) surfactant—0.1% to 0.25% (W/V).

14. The method of claim 13 wherein alcohol is present in said reagent system in an amount of between about 0.1% and 2% (V/V).

* * * * *